US00PP29988P3

(12) United States Plant Patent
Cain

(10) Patent No.: US PP29,988 P3
(45) Date of Patent: Dec. 18, 2018

(54) SWEET CHERRY TREE NAMED 'IFG CHER-TWO'

(50) Latin Name: *Prunus avium*
Varietal Denomination: IFG Cher-two

(71) Applicant: David Cain, Bakersfield, CA (US)

(72) Inventor: David Cain, Bakersfield, CA (US)

(73) Assignee: INTERNATIONAL FRUIT GENETICS, LLC, Bakersfield, CA (US)

( * ) Notice: Subject to any disclaimer, the term of this patent is extended or adjusted under 35 U.S.C. 154(b) by 19 days.

(21) Appl. No.: 15/530,573

(22) Filed: Jan. 31, 2017

(65) Prior Publication Data

US 2018/0220561 P1 Aug. 2, 2018

(51) Int. Cl.
*A01H 5/08* (2018.01)
*A01H 6/74* (2018.01)

(52) U.S. Cl.
USPC ..... Plt./181
CPC ..... *A01H 6/7445* (2018.05)

(58) Field of Classification Search
USPC ..... Plt./181
See application file for complete search history.

*Primary Examiner* — Keith O. Robinson

(57) ABSTRACT

This invention is a new and distinct sweet cherry tree denominated 'IFG Cher-two'. The new sweet cherry tree is characterized by producing large dark red fruits having broad shoulders and flat to round base. Fruits ripen early, about Apr. 14, 2014 in Delano Calif. The 'IFG Cher-two' has medium firm, medium acid fruit with a good cherry flavor. The tree has a medium low chilling requirement of approximately 300 to 500 hours. Fruits are tolerant of high summer temperatures and produce few doubled or spurred fruits.

1 Drawing Sheet

Latin name of the genus and species claimed: *Prunus avium.*

Variety denomination: 'IFG Cher-two'.

BACKGROUND OF THE INVENTION

The new and distinct sweet cherry tree described and claimed herein originated from open pollinated seeds collected in May 2001. The female parent is an unidentified sweet cherry tree growing in a commercial orchard located near Bakersfield, in Kern County, Calif. The male parent is unknown. The seeds were stratified, germinated and the resulting one seedling was planted in a field near Delano, Kern County, Calif. in April 2002. The present variety of sweet cherry tree was selected as a single plant in May 2005 and was first asexually propagated in February 2009 by grafting onto *Prunus mahalab* rootstock. It was found to reproduce true-to-type by asexual propagation. All propagation was done near Delano, Kern County Calif.

BRIEF SUMMARY OF THE INVENTION

Sweet cherries have traditionally been grown in climates with long cold winters and cool to moderately warm summers. Such climates provide enough cold winter temperatures to allow normal growth to resume in the spring and summer temperatures that are low enough not to induce production of unmarketable double or spurred fruit, but it limits the seasonality that cherries are available. The sweet cherry breeding program focuses on developing types of cherries that will grow in regions with low winter chilling and high summer temperatures so that the fruit will ripen before fruit in traditional growing regions.

The new sweet cherry tree 'IFG Cher-two' is characterized by producing large dark red fruits having broad shoulders and flat to round base. Fruits ripen early about three to five days ahead of the 'Brooks' variety (U.S. Plant Pat. No. 6,676). The 'IFG Cher-two' has medium firm, medium acid fruit with a good cherry flavor. The tree has a medium low chilling requirement slightly lower than the 'Brooks' variety. It produces fewer doubled and spurred fruits as compared to the 'Brooks' variety in high summer temperature regions such as the Southern San Joaquin Valley of Calif. Fruits of 'IFG Cher-two' have medium long, thick stems that remain attached and stay green during storage and shipping.

In comparison to the 'Brooks' variety, which is a major variety grown in warm regions, the present variety ripens about three to five days earlier and has more desirable darker red skin and flesh. It also has fewer undesirable doubled and spurred fruits as compared to 'Brooks' and has superior storage characteristics. In comparison to its female parent, the present variety has larger, firmer fruits. In comparison to the 'Tulare' variety (U.S. Plant Pat. No. 6,407), the 'IFG Cher-two' produces larger fruit that ripen approximately six to eight days before the 'Tulare' variety. The fruit shape of 'IFG Cher-two' has a more desirable flat-rounded shape with broad shoulders and flat stylar end compared to the more pointed, narrower shoulder shape of the 'Tulare' variety.

BRIEF DESCRIPTION OF THE DRAWING

The accompanying photographic illustration in FIG. 1 illustrates in full color 'IFG Cher-two', taken from a 12-year old tree. The photograph was taken outdoors with indirect lighting. The colors are as nearly true as is reasonably possible in a color representation of this type. An actively growing shoot tip collected at harvest can be seen in the upper portion of the drawing. Typical nature fruit and fruit in cross-section are displayed on the lower half of the drawing. Typical cleaned and dried fruit pits are displayed on the lower half of the drawing.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published in 2001 by The Royal Horticultural Society, London, England.

Throughout this specification subjective description values conform to those set forth by the International Board for Plant Genetic Resources (IBPGR) 'Cherry Descriptor List' (*Prunus* spp.) (1985) which was developed with full support from the Commission of the European Communities (CEC) Programme Committee for Plant Disease Resistance Breeding and the Use of Genebanks.

The descriptive matter which follows pertains to an 'IFG Cher-two' plant growing on its own roots in the vicinity of Delano, Kern County, Calif. during 2013 to 2014, and is believed to apply to plants of the variety grown under similar conditions of soil and climate elsewhere:

TREE

General:

*Age*.—12 yrs. old.
*Height*.—About 3.7 M when pruned.
*Width*.—About 3.0 M when pruned.
*Vigor*.—Vigorous.
*Density of foliage*.—Dense.
*Form*.—Upright.
*Branching*.—Medium.
*Root stock*.—Own root.
*Resistance to*.—Insects: Average typical of *Prunus avium* species. Diseases: Average typical of *Prunus avium* species.
*Chilling requirements*.—Low to Medium.
*Graft compatibility*.—Good: produces compatible graft unions with *Prunus avium*, 'Mazzard' seedling (non-patented) and *Prunus mahaleb* seedlings (non-patented).

Trunk:

*Trunk diameter of* 12-*year old trees,* 30 *cm above the soil line*.—About 18.5 cm.
*Lenticel size*.—Large.
*Lenticel dimensions*.—Length: About 1.8 cm. Width: About 0.3 cm.
*Lenticel shape*.—Elliptical shape oriented horizontally.
*Lenticel color*.—Greyed-green: 196C.
*Trunk surface*.—Rough.
*Outer bark color*.—The following colors were observed: Greyed-green: 198C and Greyed-purple: 187A.

BRANCHES 1-year old wood:

*Vertical top growth length*.—Short: About 59.7 cm.
*Horizontal growth length*.—Short: About 40.1 cm.
*Diameter*.—Vertical growth: About 1.0 cm. Horizontal growth: About 0.8 cm.
*Internode length*.—Medium: About 3.8 cm.
*Number of lenticels*.—Medium: About 6 per linear cm.
*Lenticel size*.—Small.
*Lenticel dimensions*.—Length: About 2 mm. Width: About 1 mm.
*Lenticel shape*.—Vertical, slightly oval in shape.
*Bark color*.—The following colors were observed: Greyed-orange: 175A and 177C.

2-year old wood:

*Length*.—About 50.5 cm.
*Diameter*.—About 1.1 cm.
*Internode length*.—About 4.0 cm.
*Number of lenticels*.—Medium: About 6 per linear cm.
*Lenticel size*.—Small.
*Lenticel dimensions*.—Length: About 3 mm. Width: About 1 mm.
*Lenticel shape*.—Elliptical shape oriented horizontally.
*Bark color*.—The following colors were observed: Greyed-orange: 177C and Grey: 201B.

BUDS

Vegetative buds:

*Shape*.—Oval.
*Vegetative bud dimensions*.—Length: About 1.0 cm. Width: About 1.0 cm.
*Vegetative bud burst*.—Feb. 25, 2014.

Flower buds:

*Flower bud dimensions*.—Length: About 1.0 cm. Width: About 0.4 cm.
*Shape*.—Elongated.
*Placement*.—At bud positions 1 to 10 on 1-year wood.
*Average number of flower buds on first year wood*.—About 8.
*Number of flower buds per spur on second year wood*.—2 to 3. Average: About 3.
*Color*.—The following colors were observed: Greyed-orange: 165A and 177A.
*Flower bud burst*.—Feb. 28, 2014.

LEAVES

Mature leaves:

*Leaf dimensions*.—Length: About 13.7 cm. Width: About 6.3 cm.
*Leaf shape*.—Lanceolate: symmetric on both sides of central axis.
*Shape of tip*.—Acuminate: broadly.
*Shape of base*.—Oblique.
*Margin*.—Serrated: regular: rounded.
*Leaf profile*.—Involute.

Upper surface:

*Upper surface pubescence*.—None.
*Upper leaf surface color*.—Yellow-green: 146A.
*Surface texture*.—Smooth.

Lower surface:

*Lower surface pubescence*.—Sparse to medium.
*Lower leaf surface color*.—Yellow-green: 147A.

Petiole:

*Petiole dimensions*.—Length: About 3.8 cm. Width: About 0.2 cm.
*Upper surface of petiole color*.—Red-purple: 59B.
*Lower surface of petiole color*.—The following colors were observed: Greyed-orange: 165A and 165B.
*Petiole groove*.—Medium wide: Approximately 0.7 mm.
*Petiole pubescence*.—Medium dense: only on upper surface.

*Venation*.—Arcuate.
*Vein color*.—Yellow-green: 153C.

Glands:
*Number of glands*.—2 to 3, Average: About 2.
*Gland dimensions*.—Length: About 2.0 mm. Width: About 2.0 mm.
*Gland shape*.—Mixed globose and reniform.
*Gland location*.—On petiole.
*Gland color*.—Red-purple: 60A.
*Leaf stipule*.—Not present.

Flowers:
*Blooming period*.—Early.
*Blooming dates*.—First bloom: Mar. 4, 2014. Full bloom: Mar. 18, 2014.
*Number of flowers per cluster*.—2 to 4. Average: About 3.
*Corolla*.—Composed of unfused petals, somewhat overlapping.
*Corolla diameter*.—About 3.0 cm.
*Petal number*.—5.
*Petal length*.—About 1.5 cm.
*Petal width*.—About 1.5 cm.
*Margin waviness*.—Strong.
*Division of upper margin*.—Notched.
*Color of petal upper surface*.—The following colors were observed: White: N155C and D.
*Color of petal lower surface*.—The following colors were observed: White: N155C and D.
*Peduncle*.—Length: About 1.5 cm. Width: About 0.2 cm.
*Peduncle color*.—Yellow-green: 144A.
*Number of sepals*.—5.
*Sepal length*.—About 0.6 cm.
*Sepal width*.—About 0.5 cm.
*Sepal shape*.—Ovate.
*Sepal color*.—The following colors were observed: Upper surface: Yellow-green: 144D and 145A. Lower surface: Greyed-purple: 183B and C.
*Filament*.—Length: About 0.6 to 1.4 cm. Width: About 0.3 mm.
*Filament color*.—The following colors were observed: White: 155B and C and D.
*Anther color*.—The following colors were observed: Grey-orange: 163B and C.
*Pollen color*.—Greyed-orange: 163A.
*Pollen production*.—Medium.
*Self-compatibility of flowers*.—Self-incompatible.
*Flower compatibility group*.—S9S new unidentified allele.

FRUIT

General:
*Ripening period*.—Early: Approximately: Apr. 24, 2014.
*Use*.—Fresh market.
*Keeping quality*.—Average: Similar to 'Brooks' variety.
*% Titratable acidity*.—About 0.92%.
*Refractometer test*.—Soluble solids; Brix — About 17.8.
*Firmtech II (g/mm)*.—About 303.
*Flavor*.—Sweet with medium acidity and good cherry flavor.
*Juice color*.—Red: 47A.
*Juice amount*.—Juicy.
*Eating quality*.—Good.

Stem:
*Stem*.—Length: About 2.6 cm. Width: About 0.2 cm.
*Stem color*.—Yellow-green: 144B.
*Stem cavity*.—Medium deep.
*Stem retention during storage*.—Very good, superior to 'Brooks'.
*Stem storage quality*.—Good, superior to 'Brooks'.

Berry:
*Uniformity of size*.—Uniform.
*Shape*.—Flat-round.
*Fruit weight*.—About 9.2 gm.
*Apical diameter*.—About 2.3 cm.
*Diameter transversely across suture*.—About 2.8 cm.
*Diameter at right angle to suture plane*.—About 2.2 cm.
*Suture*.—None.
*Percent of excessively deep or split sutures*.—About 0.0%.
*Doubles*.—About 0.0%.

Skin:
*Texture*.—Smooth, tender.
*Skin color*.—Greyed-purple: 187A.
*Tendency to tip crack*.—Not susceptible.
*Tendency to stem cavity crack*.—Not susceptible.

Flesh:
*Texture*.—Medium firm.
*Color*.—The following colors were observed: Greyed-purple: 187C and Red-purple: 59D.

Stone:
*Stone dimensions*.—Length. About 11 mm. Width: About 8 mm.
*Type*.—Freestone.
*Surface texture*.—Smooth.
*Stone color when dry*.—Orange-white: 158A.
*Tendency to split*.—None.
*Shape*.—Spherical to slightly ovate.
*Base*.—Rounded.
*Apex*.—Broadly pointed.
*Ventral edge*.—Minimal, flat suture subtended by 2 ridges converging at base and apex.
*Dorsal edge*.—Smooth, narrow ridge from base to apex.

What is claimed:

1. A new and distinct variety of sweet cherry tree as herein illustrated and described.

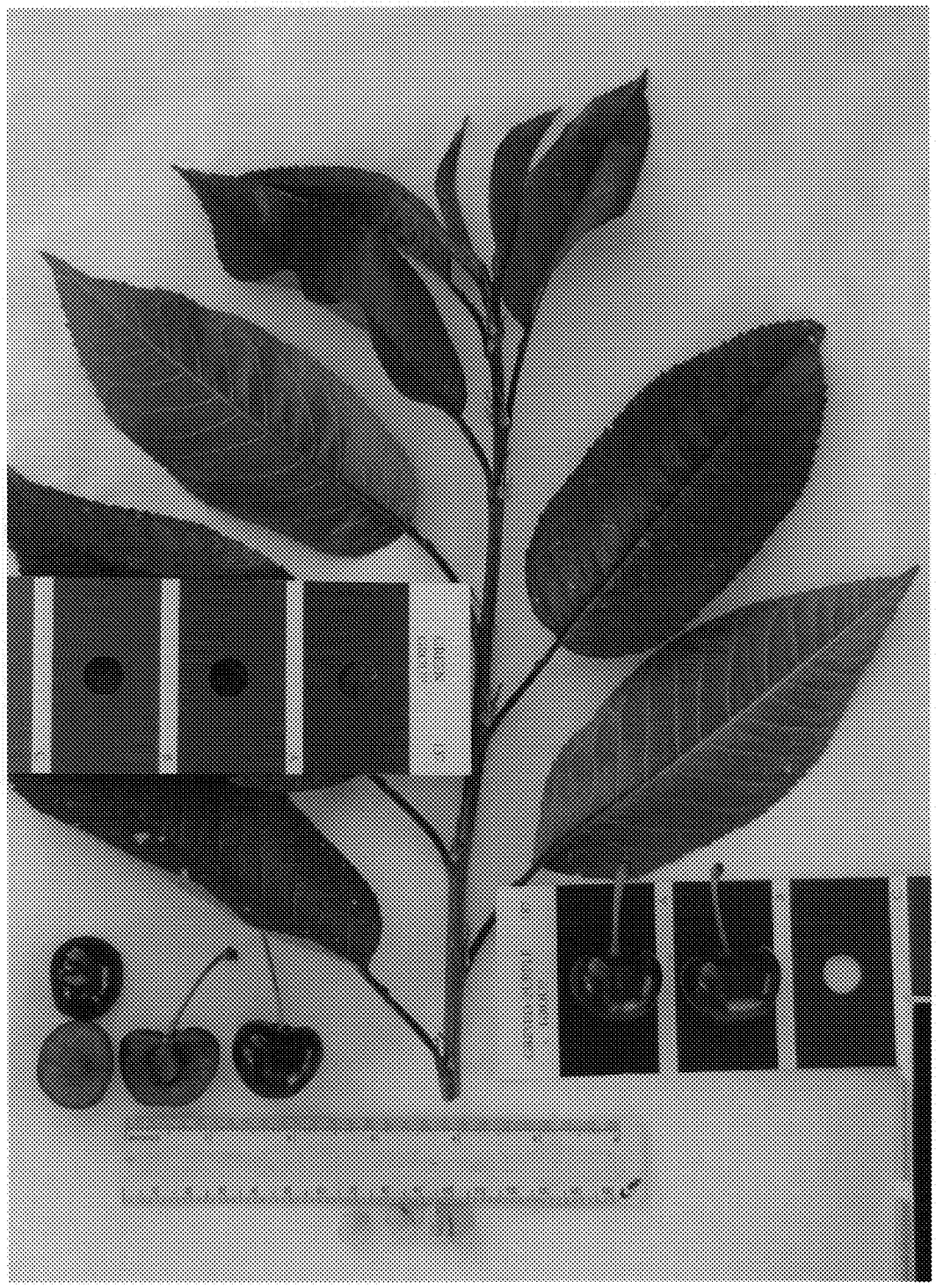

* * * * *